(12) United States Patent
Shay

(10) Patent No.: US 6,598,618 B1
(45) Date of Patent: Jul. 29, 2003

(54) FLOW REGULATOR

(75) Inventor: Ofer Shay, Kfar Vradim (IL)

(73) Assignee: P.M.P. Precise Medical Products Ltd., Shlomi (IL)

( * ) Notice: Subject to any disclaimer, the term of this patent is extended or adjusted under 35 U.S.C. 154(b) by 0 days.

(21) Appl. No.: 09/857,484

(22) PCT Filed: Nov. 29, 1999

(86) PCT No.: PCT/IL99/00643

§ 371 (c)(1), (2), (4) Date: Jul. 23, 2001

(87) PCT Pub. No.: WO00/33896

PCT Pub. Date: Jun. 15, 2000

(30) Foreign Application Priority Data

Dec. 6, 1998 (IL) .................................................. 127406

(51) Int. Cl.⁷ ................................................. G05D 7/01
(52) U.S. Cl. ........................ 137/501; 251/121; 251/337
(58) Field of Search ................................. 137/501, 504; 251/121, 337

(56) References Cited

U.S. PATENT DOCUMENTS

| | | | | |
|---|---|---|---|---|
| 4,241,757 A | * | 12/1980 | Bron | 137/501 |
| 5,101,854 A | * | 4/1992 | Bron | 137/501 |
| 5,421,363 A | * | 6/1995 | Bron | 137/501 |

* cited by examiner

*Primary Examiner*—Stephen M. Hepperle
(74) *Attorney, Agent, or Firm*—Eitan, Pearl, Latzer & Cohen Zedek, LLP.

(57) ABSTRACT

The invention relates to a variable flow regulator adopted to provide accurate flow rates at low flow and ultra low flow rates. The regulator comprises a wide-range flow regulator for low fluids flow, comprising a housing divided into a first and second chambers by means of an elastic diaphragm. The chamber is provided with a fluid inlet and an outlet connected to a labyrinth path.

28 Claims, 4 Drawing Sheets

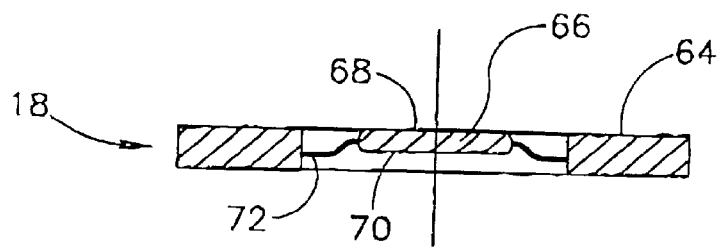
FIG.2
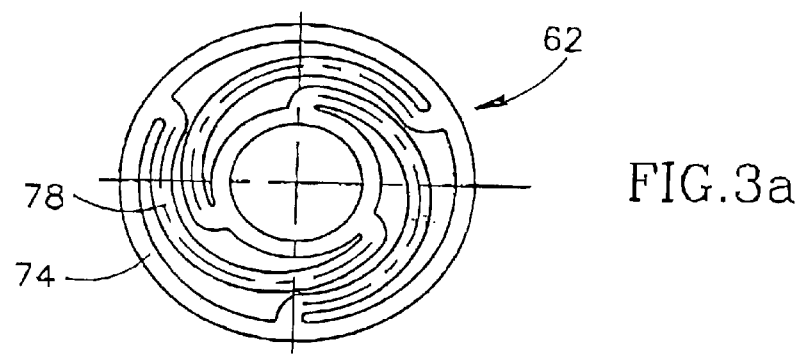
FIG.3a
FIG.3b
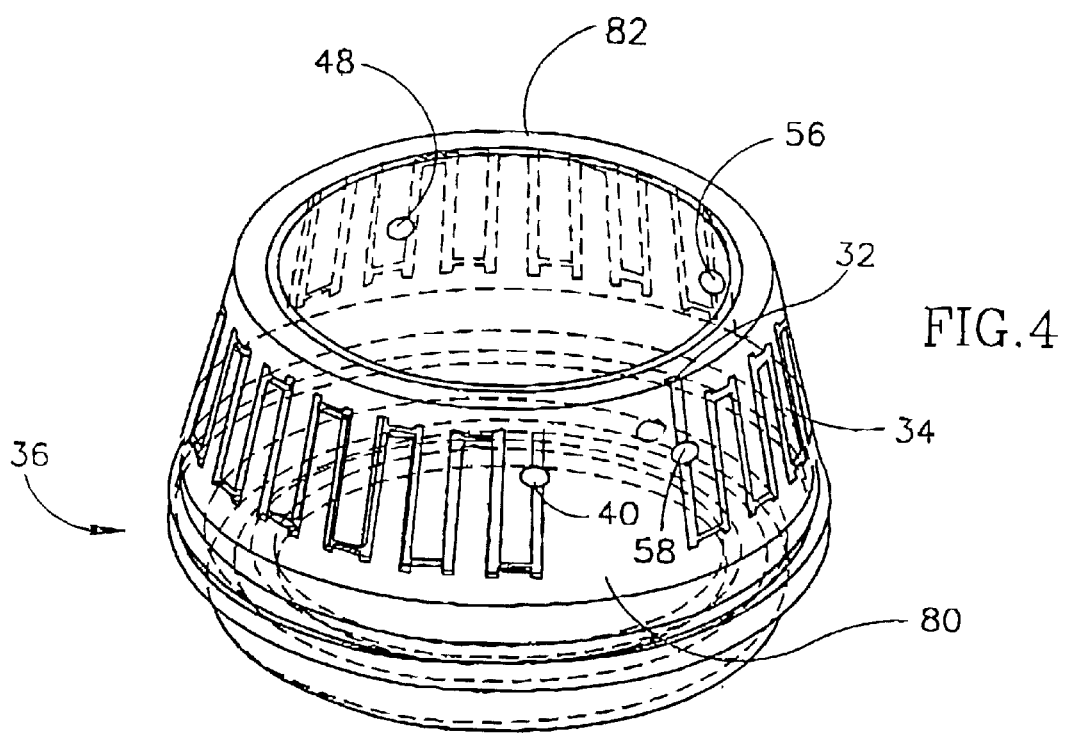
FIG.4

FLOW REGULATOR

The present invention relates to the control of low fluid flows.

More particularly, the invention provides a variable flow regulator able to provide accurate flow rates, at low flow and ultra low flow rates, typically as required in medical and laboratory applications.

In hospitals and clinics medicines and other fluids are administered to patients for a variety of purposes. Most common is the administration of infusions to patients who are dehydrated or not eating and drinking for a variety of reasons. Flow rates can be adjusted according to the needs of the patient, typically in the range 100–500 ml per hour.

Medicines not taken by mouth can be added to an infusion, or are injected by the use of a syringe having a hollow needle, the contents of a 5 to 25 ml ampoule being received by the patient in 2–5 seconds.

These methods cannot be utilized where medical fluids are to be received by the patient at controlled and very slow feed rates, typically under 10 ml per hour, Such time-extended flow requires a source of power other than the finger pressure of a medical attendant on a syringe plunger. The power source can be gravity or an elastic element, in combination with a flow regulator, or an electrically driven pump can be used with or without a flow regulator.

Certain patients receive medication, for example insulin, from devices carried on their body in a belt pouch or clothing pocket. Portable devices, normally powered by electric batteries, can serve this purpose.

Adjustable flow, mains electricity-driven metering pumps are used in industrial and chemical applications, and for dispensing, for example, liquid fertilizers, chlorine and fluoride. A positive displacement peristaltic pump of this type marketed under the MECOMATIC trade name can be adjusted down to 0.25 gallons per day. Although the tubing can be readily changed, this pump weighs 9.5 lb. and is obviously not disposable, and such pumps are not suitable for medical applications requiring extremely slow flow rates.

In U.S. Pat. No. 4,544,369 Skakoon et al disclose a battery-operated miniature syringe infusion pump. The device includes a battery, a DC motor, gearing, electronic controls, a lead screw, a force-sensing system, indicators, and alarms and is light enough to be mounted on an IV pole. The main drawbacks are high initial costs, lack of portability and the need for batteries. U.S. Pat. No. 5,034,004 to Crankshaw is generally similar to the Skakoon specification but involves even more mechanical and electronic components.

A less complex arrangement is disclosed in U.S. Pat. No. 4,976,696, which specification includes control means for regulating the movement of a driver against the syringe plunger. It is however uncertain whether the very slow flow rates which are a main feature of the present invention can be handled merely by controlling plunger movement, and without the use of a further fluid resistor.

It is therefore one of the objects of the present invention to obviate the disadvantages of prior art flow regulators and to provide a device which can reliably deliver low flows and very low flows.

It is a further object of the present invention to provide a regulator which can be adjusted within a wide range in its capacity.

Yet a further object of the present invention is to provide a self-powered regulator for delivering fluids at very low flow rates.

The present invention achieves the above objects by providing a wide-range flow regulator for low fluid flows, comprising a housing divided into a first and a second chamber by means of an elastic diaphragm, said first chamber having an inlet for a fluid, and an outlet connected to a labyrinth path.

The second chamber has an inlet connected to an outlet of said labyrinth path, the outlet of said second chamber being an inlet at an extremity of a discharge tube, the discharge tube inlet being positionable at a short distance from the diaphragm.

Means are provided to vary said distance to achieve fine adjustment of the flow rate, the discharge tube inlet being sealed by the diaphragm when said diaphragm flexes in response to pressure drop in the second chamber. The labyrinth path connects the first chamber to the second chamber to allow the liquid to flow under controlled pressure drop from the first chamber to the second chamber and so to intermittently raise pressure in the second chamber to temporarily separate the diaphragm from the discharge tube inlet. This allows liquid to enter and traverse the discharge tube for use of said fluid.

Means are provided to selectively short-circuit at least a portion of the labyrinth path to vary the range of the fluid flow rate.

In a preferred embodiment of the present invention there is provided a flow regulator wherein the inlet of said first chamber is connectable to receive fluid by gravitational means.

In a most preferred embodiment of the present invention there is provided a flow regulator wherein said inlet of the first chamber is connectable to receive fluid from a syringe.

Yet further embodiments of the invention will be described hereinafter

In U.S. Pat. No. 5,421,363 Bron describes and claims an adjustable-rate flow regulator intended for use between an infusion bag and a tube leading to a patient. The device relies entirely on changing the used length of the labyrinth in order to effect changes in the flow rate. Changes in the length of the labyrinth are effective for coarse adjustment, but less effective for fine adjustment. Total reliance on labyrinth length will not ensure accuracy, as slight viscosity changes in the fluid, for example as result of temperature variations, will result in substantial flow variation.

A further disadvantage of total reliance on the labyrinth lies in the fact that the covered range is limited. Tests carried out with plastic drip irrigation tubing have shown that where the labyrinth is long, substantial labyrinth length changes result in only marginal changes in flow rates.

Furthermore, the performance of the Bron device is dependent on the stiffness of the flexible diaphragm. Such stiffness can vary widely with conditions of age, humidity and exposure to chemical attack.

In contradistinction thereto, the present invention, in addition to labyrinth length adjustment, also provides means for fine adjustment of flow rates, by providing means for adjusting the distance between the diaphragm and the inlet of the discharge tube. Consequently the device of the present invention can be used over a very wide range, typically from 1 to 200 ml per hour. The stiffness of the diaphragm has little effect on performance, as a spring provides the force needed to press the diaphragm into contact with the regulator inlet It will also be realized that the novel regulator of the present invention can be mass produced by plastic injection molding of its individual parts and that assembly of the components can be effected in very little time—easily in less than a minute. Consequently the device can be marketed for disposable use, as is preferred for medical applications.

The invention will now be described further with reference to the accompanying drawings, which represent by example preferred embodiments of the invention. Structural details are shown only as far as necessary for a fundamental understanding thereof. The described examples, together with the drawings, will make apparent to those skilled in the art how further forms of the invention may be realized.

In the Drawings:

FIG. 2 is a sectional elevation of a diaphragm used in the regulator;

FIGS. 3a & 3b are plan and sectional views of a spring used in the regulator;

FIG. 4 is a perspective view of the conical member carrying the labyrinth path;

Figure 1:
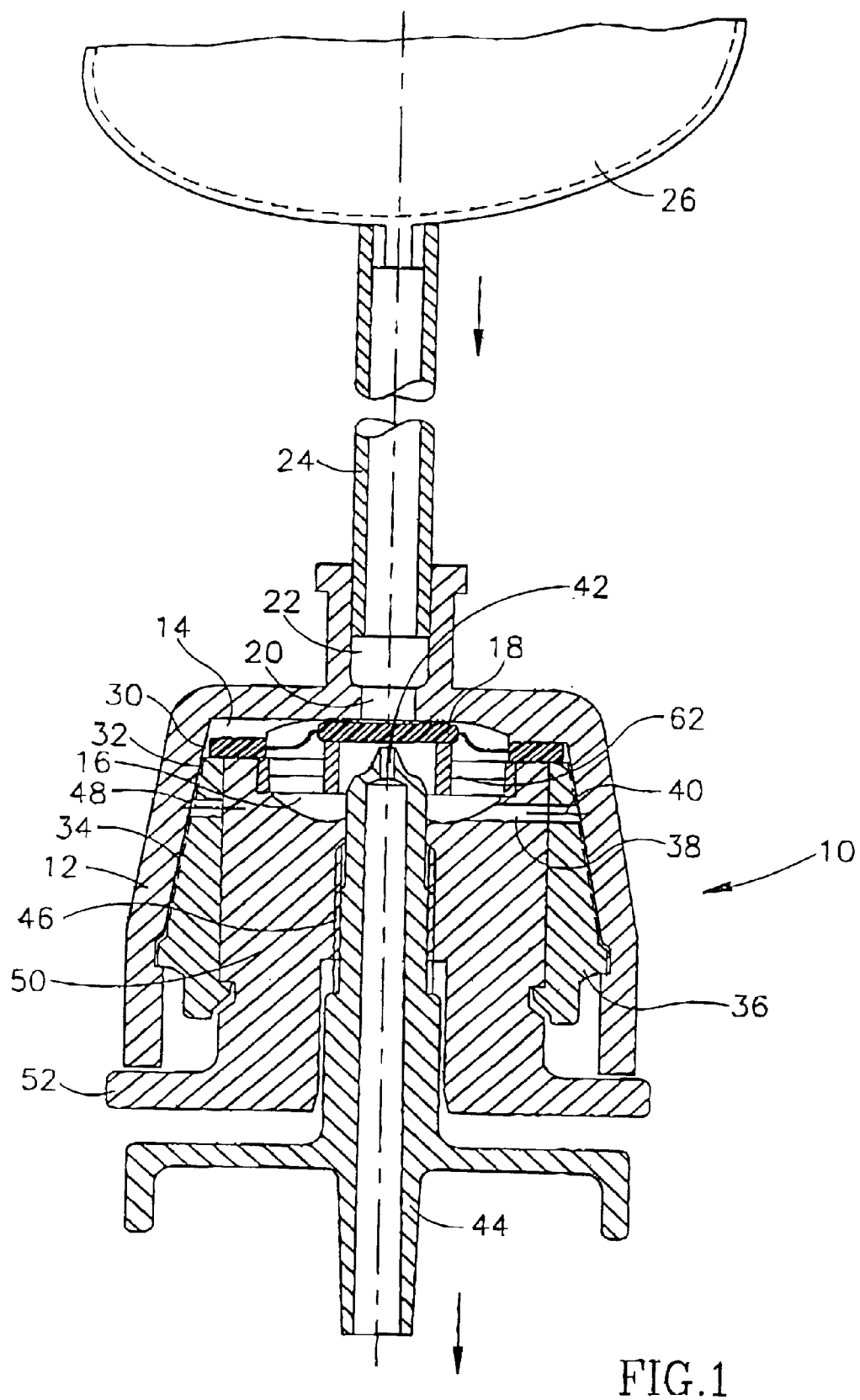
FIG. 1 is a sectional elevation of a preferred embodiment of the low flow regulator according to the invention.

There is seen in FIG. 1 a wide-range flow regulator 10 for low fluid flows.

The regulator 10 is contained in a housing 12, which is divided into a first 14 and a second chamber 16 by means of an elastic diaphragm 18.

The housing 12 is suitably made of a hard plastic, for example ABS.

The first chamber 14 has an upper inlet 20 for a fluid, this inlet being connected to a tapered mouth 22. In the present embodiment, the inlet 20 is connected to receive fluid by gravitational means, using a tube 24 connected to a fluid supply such as a suspended medical infusion bag 26.

In the gravity feed mode of the present embodiment, fluid flow is adjustable between about 10 to about 200 ml per hour.

The outlet from the first chamber 14 in the present embodiment comprises a gap 30 between the diaphragm 18 outer diameter and the housing 12, allowing fluid to enter an upper inlet 32 of a labyrinth path 34 formed in the outer face of a hollow conical member 36, seen more clearly in FIG. 4.

The second chamber 16 has an inlet aperture 38 alignable to a full path length outlet 40 of the labyrinth path 34. The outlet of the second chamber 16 comprises an inlet 42 at an extremity of a discharge tube 44.

The discharge tube inlet 42 is positionable at a short distance from the diaphragm 18. Means such as the screw thread 46 shown are provided to vary this distance, thereby to achieve fine adjustment of the flow rate. Reducing this distance reduces flow rate, an increase increases flow.

The discharge tube inlet 42 is sealed by the diaphragm 18 when the diaphragm flexes downwards in response to pressure drop in the second chamber 16.

The labyrinth path 34 connects the first chamber 14 to the second chamber 16 to allow the liquid to flow under controlled pressure drop from the first chamber 14 to the second chamber 16. Such flow intermittently raises pressure in the second chamber 16, and temporarily separates the diaphragm 18 from the discharge tube inlet 42. This allows fluid to enter and traverse the discharge tube 44 for use of the fluid.

To prime the regulator 10 for use, air is removed by allowing free flow through the discharge tube 44.

Means, such as intermediate apertures 48, and 56 seen in FIG. 4, through the labyrinth path 34 are provided to selectively short-circuit at least a portion of the labyrinth path 34 to vary the range of the fluid flow rate.

Figure 6:
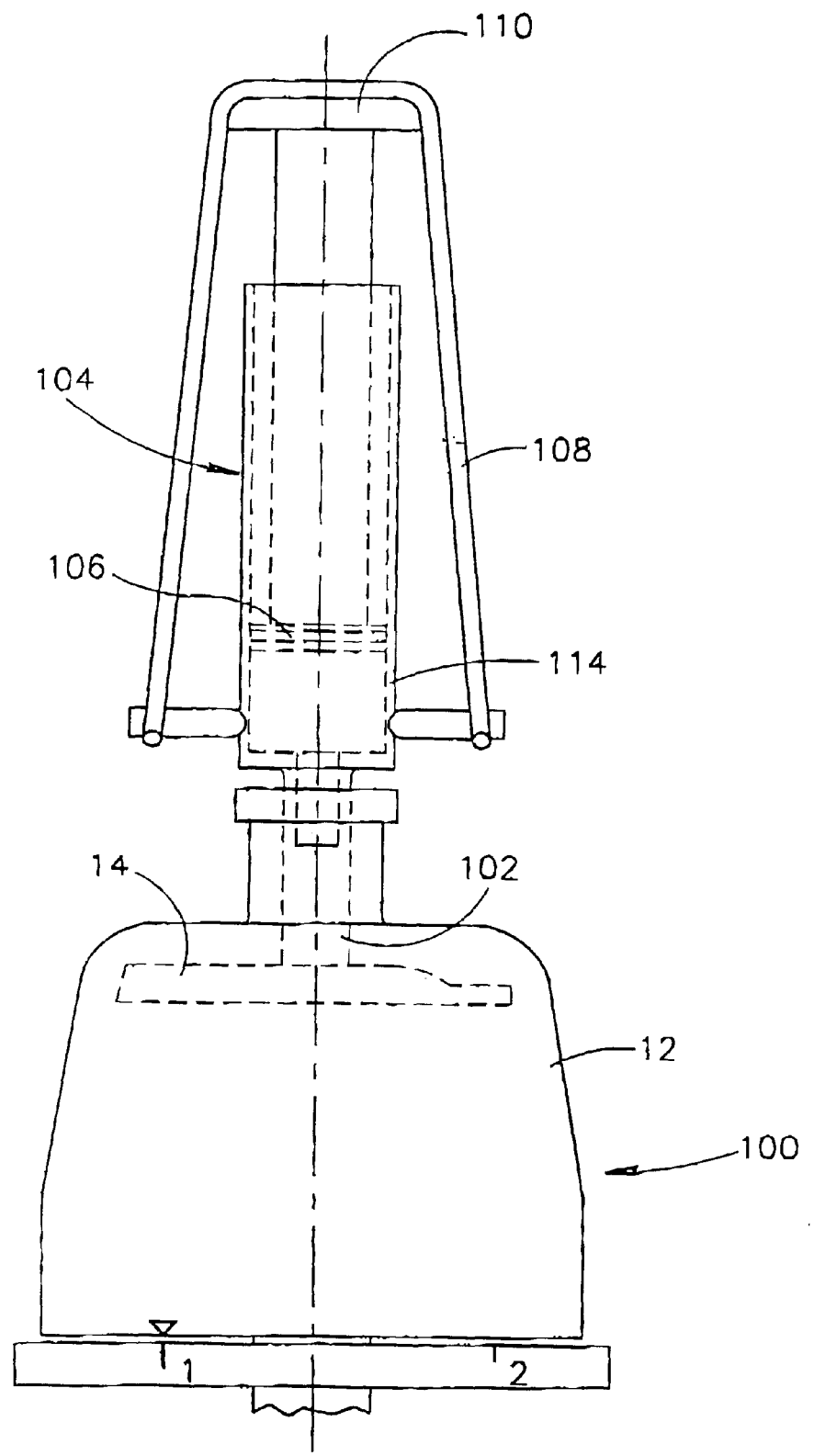
FIG. 6 is an elevational view of a powered syringe connected to a very low flow regulator.

A revolvable seal flange 50 is accessible to the user by means of its projecting outer diameter 52. The user may thus turn the seal flange 50 relative to the hollow conical member 36 and housing 12; the latter two components retain a fixed relationship to each other. The seal flange 50 carries the inlet aperture 38 which is alignable with alternate outlet apertures 40, 48, 56, of the labyrinth path 34. When so aligned fluid may enter the second chamber 16, such fluid having passed along only a part of the labyrinth path if an intermediate outlet aperture is aligned to the inlet aperture 38. Scale markings 60, seen in FIG. 6, are provided to guide the user in this adjustment.

When preparing the regulator 10 for use it is advantageous to use provided means to selectively short-circuit the whole of the labyrinth path 34 to allow fast air evacuation of the regulator and of elements connected thereto. This is achieved when the labyrinth aperture 58, seen in FIG. 4, is aligned with the seal flange inlet aperture 38.

The seal flange 50 is made of a medium hardness plastic, for example a polyester.

Preferably a spring 62, to be described with reference to FIG. 3, urges the diaphragm 18 away from the discharge tube inlet 42.

The regulator 10 is advantageously configured for disposable use. Its components are designed for plastic injection molding to allow low cost high volume economic manufacture.

In summary, the fluid path in the present embodiment is as follows:

Infusion bag 26
Tube 24
Upper inlet 20
First chamber 14
Diaphragm by-pass gap 30
Labyrinth upper inlet 32
Labyrinth path 34
Labyrinth full path exit aperture 40
Second chamber inlet aperture 38
Second chamber 16
Discharge tube inlet 42
Discharge tube 44
User With reference to the rest of the figures, similar reference numerals have been used to Identify similar parts.

Referring now to FIG. 2, there is seen a diaphragm 18 having a thick outer ring 64 serving as a seal element.

A central disk 66 has a first 68 and a second opposite face 70. When assembled in the regulator 10, first face 68 is in proximity to the first chamber upper inlet 20.

The second face 70 is configured to seal the discharge tube inlet 42.

A thin flexible section 72 connects outer ring 64 and central disk 66. The flexible section can withstand bending without high strain due to being only about 0.5–1 mm thick. The low strain improves reliability of this component.

The diaphragm 18 is suitably made of a silicon elastomer.

FIGS. 3a & 3b illustrate a spring 62, which when in use urges diaphragm 18 away from discharge tube inlet 42.

The spring 62 comprises an outer ring 74 retained in second chamber 16, a central disk 76 configured to press against the central disk 66 of the diaphragm 18, and a plurality of curved arms 78 connecting outer ring 74 and central disk 76.

The special form of spring 62 makes possible the exertion of a high force in the small space available for its operation. Suitable materials therefore are stainless steel and ABS.

Seen in FIG. 4 is the hollow conical member 36 previously seen in FIG. 1. The labyrinth path 34 comprises an open channel disposed on the outer face 80. When in use, the member 36 is positionally fixed inside housing 12 so allowing the conical inner face of housing 12 to provide a leak-proof seal for the open face of the labyrinth path 34.

The labyrinth path inlet 32 extends to the upper edge 82 of the member 36. Adjacent to inlet 32 is a short circuiting outlet, labyrinth aperture 58 used during priming. Intermediate outlets are seen at 48.and 56. When minimum flow rates are required, the full length of the labyrinth path is used and fluid exits the labyrinth path 34 through aperture 40.

The hollow conical member 36 is suitably made of hard technical plastic material.

Figure 5:
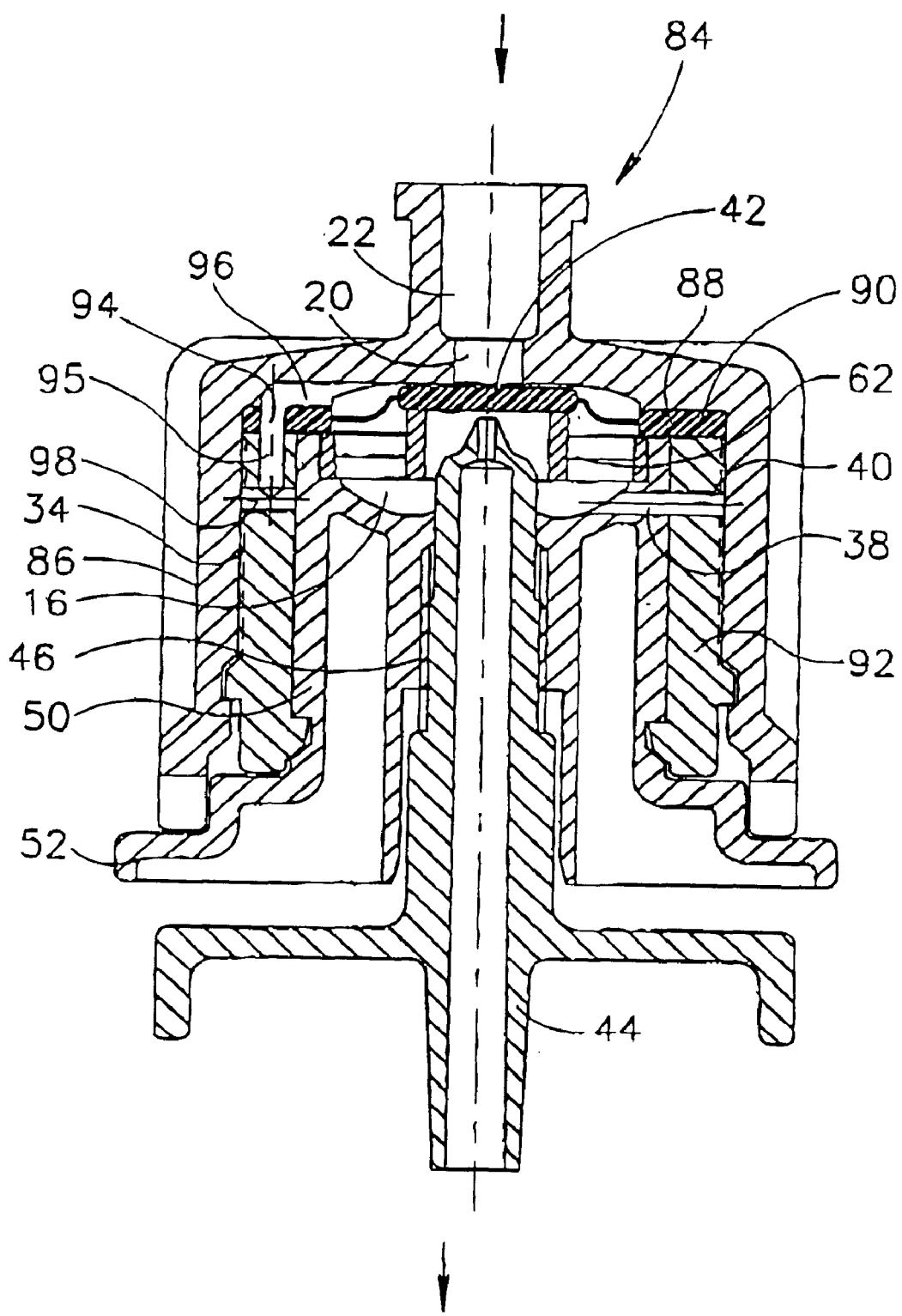
FIG. 5 is a sectional elevation of a second embodiment of the regulator.

Referring now to FIG. 5, there is depicted a further embodiment 84 of the flow regulator, which is similar to 10 except as will be described.

The included angle of conical member outer face 86 is between 176 and 179 degrees, which is a convenient angle for manufacturing purposes.

The diaphragm 88 completely covers the upper edge 90 of the hollow conical member 92, without leaving any gap. However an aperture 94 in the diaphragm 88, and an aligned aperture 95 in the hollow conical member 92 allows fluid to flow from the first chamber 96 to the entrance 98 of the labyrinth path 34.

FIG. 6 shows a flow regulator 100 similar to that shown in FIG. 1, wherein the upper inlet 102 of first chamber 14 is connected to receive fluid from a syringe 104. Typically such syringe has a capacity of 50–60 ml.

Advantageously syringe 104 is provided with means urging the syringe piston 106 towards first chamber upper inlet 102. Such means in this embodiment comprises a tensioned elastic element 108 disposed between an exposed extremity 110 of piston 106 and anchor elements 112 attached to the syringe body 114.

Typically fluid flow is adjustable between about 1 to about 10 ml per hour.

In the shown embodiment the syringe 104 is shown as a separate but connected unit, this being advantageous in allowing the use of a standard low-cost syringe. Nevertheless it will be understood that the syringe body 114 and the regulator housing 12 can be manufactured if required as one integral unit.

In operation the regulator 100 is primed while short-circuiting the labyrinth path 34 as explained with reference to FIG. 1. The syringe 104 is then filled, connected to the regulator 100, and air is discharged from the regulator as the elastic element 108 applies pressure on the syringe piston 106 to initiate fluid flow. Flow rate is then adjusted to a desired flow rate as explained with reference to FIG. 1.

The scope of the described invention is intended to include all embodiments coming within the meaning of the following claims. The foregoing examples illustrate useful forms of the invention, but are not to be considered as limiting its scope, as those skilled in the art will readily be aware that additional variants and modifications of the invention can be formulated without departing from the meaning of the following claims.

What is claimed is:

1. A wide-range flow regulator for low fluid flows, comprising:
    a housing comprising first and second chambers, said first and second chambers each having an inlet and an outlet, said outlet of said first chamber and said inlet of said second chamber connected by a labyrinth path;
    an at least partly elastic diaphragm separating said first chamber and said second chamber, said diaphragm comprising an outer ring, a central disk, and an intermediate section connecting said outer ring and said central disk, wherein said intermediate section is more flexible than said central disk; and
    a discharge tube having an inlet connected to said outlet of said second chamber,
    wherein the central disk of said diaphragm seals the inlet of said discharge tube when there is a change in the pressure differential between said second chamber and said first chamber.

2. The flow regulator as in claim 1, further comprising a planar spring having an outer ring retained in said second chamber, an inner disk configured to press against said diaphragm, and a plurality of curved arms connecting said outer ring and said inner disk.

3. The flow regulator according to claim 1, further comprising short-circuit means to selectively short-circuit at least a portion of said labyrinth path.

4. A flow regulator according to claim 3, wherein said short-circuit means to selectively short-circuit at least a portion of said labyrinth path comprises a revolvable seal flange, said seal flange having a transfer aperture alignable with intermediate points along said labyrinth path.

5. The flow regulator as claimed in claim 3, wherein said short-circuit means comprises means to selectively short-circuit the entire said labyrinth path.

6. The flow regulator as in claim 1, further comprising positioning means for controlling the distance between said inlet of said discharge tube and said diaphragm.

7. A flow regulator according to claim 1, being configured for disposable use.

8. A flow regulator according to claim 1, wherein said inlet of said first chamber is connectable to a suspended medical infusion bag.

9. A flow regulator according to claim 8, wherein fluid flow from said infusion bag is adjustable between about 1 to about 200 ml per hour.

10. A wide-range flow regulator for low fluid flows, comprising:
    a housing comprising first and second chambers, said first and second chambers each having an inlet and an outlet, said outlet of said first chamber and said inlet of said second chamber connected by a labyrinth path;
    an at least partly elastic diaphragm separating said first chamber and said second chamber;
    a planar spring comprising an outer ring retained in said second chamber, an inner disk configured to press against said diaphragm, and a plurality of curved arms connecting said outer ring and said inner disk; and
    a discharge tube having an inlet connected to said outlet of said second chamber;
    wherein said diaphragm seals the inlet of said discharge tube when there is a change in the pressure differential between said second chamber and said first chamber.

11. The flow regulator according to claim 10, further comprising short-circuit means to selectively short-circuit at least a portion of said labyrinth path.

12. A flow regulator according to claim 11, wherein said short-circuit means to selectively short-circuit at least a portion of said labyrinth path comprises a revolvable seal flange, said seal flange having a transfer aperture alignable with intermediate points along said labyrinth path.

13. The flow regulator as claimed in claim 11, wherein said short-circuit means comprises means to selectively short-circuit the entire said labyrinth path.

14. The flow regulator as in claim 10, further comprising positioning means for controlling the distance between said inlet of said discharge tube and said diaphragm.

15. A flow regulator according to claim 10, being configured for disposable use.

16. A flow regulator according to claim 10, wherein said inlet of said first chamber is connectable to a suspended medical infusion bag.

17. A flow regulator according to claim 16, wherein fluid flow from said infusion bag is adjustable between about 1 to about 200 ml per hour.

18. A wide-range flow regulator for low fluid flows, comprising:

- a housing comprising first and second chambers, said first and second chambers each having an inlet and an outlet, said outlet of said first chamber and said inlet of said second chamber connected by a labyrinth path, said labyrinth path comprising an open channel disposed on the outer face of a hollow member and confined by the inner face of said housing;
- an at least partly elastic diaphragm separating said first chamber and said second chamber; and
- a discharge tube having an inlet connected to said outlet of said second chamber at a distance from said diaphragm;
- wherein said diaphragm seals the inlet of said discharge tube when there is a change in the pressure differential between said second chamber and said first chamber.

19. A flow regulator according to claim 18, further comprising:

- an aperture in said diaphragm; and
- an aperture in said hollow member, wherein said aperture in said hollow member is aligned with said aperture in said diaphragm.

20. The flow regulator as claimed in claim 18, wherein said hollow member is conical.

21. The flow regulator as claimed in claim 20, wherein an outer face of said hollow member has an included angle of between 176 and 179 degrees.

22. The flow regulator according to claim 18, further comprising short-circuit means to selectively short-circuit at least a portion of said labyrinth path.

23. A flow regulator according to claim 22, wherein said short-circuit means to selectively short-circuit at least a portion of said labyrinth path comprises a revolvable seal flange, said seal flange having a transfer aperture alignable with intermediate points along said labyrinth path.

24. The flow regulator as claimed in claim 22, wherein said short-circuit means comprises means to selectively short-circuit the entire said labyrinth path.

25. The flow regulator as in claim 18, further comprising positioning means for controlling the distance between said inlet of said discharge tube and said diaphragm.

26. A flow regulator according to claim 18, being configured for disposable use.

27. A flow regulator according to claim 18, wherein said inlet of said first chamber is connectable to a suspended medical infusion bag.

28. A flow regulator according to claim 27, wherein fluid flow from said infusion bag is adjustable between about 1 to about 200 ml per hour.

* * * * *